United States Patent [19]

Curran

[11] Patent Number: 4,771,326

[45] Date of Patent: Sep. 13, 1988

[54] COMPOSITION DOUBLE HETEROJUNCTION TRANSISTOR

[75] Inventor: Patrick A. Curran, Plano, Tex.

[73] Assignee: Texas Instruments Incorporated, Dallas, Tex.

[21] Appl. No.: 883,876

[22] Filed: Jul. 9, 1986

[51] Int. Cl.[4] .................. H01L 29/72; H01L 29/04; H01L 29/54; H01L 29/12

[52] U.S. Cl. ........................ 357/34; 357/16; 357/4; 357/56; 357/60; 357/61; 357/15; 357/63

[58] Field of Search .............. 357/16, 34, 4, 56, 60, 357/61, 15, 63

[56] References Cited

U.S. PATENT DOCUMENTS

| | | | |
|---|---|---|---|
| 3,211,970 | 10/1965 | Christian | 357/16 |
| 4,062,034 | 12/1977 | Matsushita et al. | 357/2 |
| 4,302,763 | 11/1981 | Ohuchi et al. | 357/16 |
| 4,482,910 | 11/1984 | Nishizawa et al. | 357/34 |
| 4,661,829 | 4/1987 | Bean et al. | 357/30 |

Primary Examiner—Andrew J. James
Assistant Examiner—John Lamont
Attorney, Agent, or Firm—Gary C. Honeycutt; Melvin Sharp; N. Rhys Merrett

[57] ABSTRACT

A heterojunction transistor has an acceptor doped superlattice base of sub-micron thickness, a composite emitter with a donor concentration adjacent the base, with a wider bandgap energy than the base, and with a low recombination velocity to minimize minority carrier diffusion and to set the divergence of emitter and base carrier velocities, and a collector configured like the emitter, permitting control and optimization of the cut-in voltage. The method for making the transistor includes forming the base, emitter, and collector by non-compensated, non-planar wafer processing techniques.

14 Claims, 2 Drawing Sheets

COMPOSITION DOUBLE HETEROJUNCTION TRANSISTOR

BACKGROUND OF THE INVENTION

1. Field of the Invention

This invention relates to improvements in heterojunction transistors and methods for making same, and more particularly to an improved heterojunction transistor which has controllable base-emitter diode cut-in voltages, controllable offset voltages, and increased gain than predicted by classical transistor theories, and to a method for making same.

2. Description of the Prior Art

In 1950, U.S. Pat. No. 2,569,347 issued to Shockley, a wide bandgap emitter heterojunction transistor with improved gain and performance was disclosed. Since then, much work has been expended to realize the full theoretical potential of this type transistor, but without total success.

Today, it is known that semiconductor bandgap energy is the energy required to create a hole-electron pair by exciting a mobile hole into the valence band and a mobile electron into the conduction band. Two methods of creating mobile carriers in the respective bands are by creating mobile hole-electron pairs and by introducing impurity atoms which create a mobile carrier in one band with a residue ionized lattice atom. The mobile carriers created by these two methods are distinctly different.

By the hole-electron pair method, a mobile electron is excited into the conduction band and a corresdponding mobile hole into the valence band, with a corresponding increase in potential energy (less negative lattice energy). The mobile electrons and holes in this case always exist in pairs, termed excitons.

By the impurity atom introduction method, impurity atoms are introduced near one of the two bands, to create mobile carriers at very low temperatures prior to exciton formation. For instance, donor impurities are located near the conduction band and acceptor impurities are located near the valence band. In silicon, for example, acceptor impurities are trivalent atoms, like boron or gallium, and donor impurities are pentavalent atoms, like phosphorous or arsenic. Ionized mobile carriers never occur in pairs between the conduction and valence bands, but are always coupled to the ionized impurity atoms. The pairs of ionized impurity atoms and ionized mobile carriers are termed polarons.

The chemostatic potential of a semiconductor region is related to the polaron/exciton ratio for usable energy ranges. Specifically, the chemostatic potential energy is $$kT\ln(N/n_i)$$

for $N \gg n_i$, where $N$ is the net ionized impurity concentration and $n_i$ is the intrinsic carrier concentration. The intrinsic carrier concentration is, among other things, a measure of the bandgap energy. In steady-state, excitons are generated and recombined at identical rates, the recombination rate. The inverse of the recombination rate, normalized with respect to the exciton concentration, is the exciton lifetime, or the statistical duration of an exciton before hole-electron pair annihilation. The inverse of the exciton lifetime gradient is the recombination velocity, which is the measure of the spatial recombination rate variation. Diffusion can only exist in the presence of a non-zero recombination velocity, that is, a spatially variable recombination rate, and the propensity to diffuse is enhanced by increasing recombination velocity.

The total chemostatic potential energy is a measure of the potential energy available to support the transport of minority carriers by diffusion. Greater chemostatic potential energy magnitude manifests larger potential recombination velocity, which can result in larger diffusion currents. Mobile electron diffusion is favored for large positive chemostatic potential energy, while mobile hole diffusion is favored for large negative chemostatic potential energy. Thus, in a bipolar transistor, it is highly desirable to have a very large chemostatic potential energy magnitude in the base region to enhance minority carrier transport through the base. Although the chemostatic potential is a relative measure of polarons and excitons, a secondary diffusion effect depends on the absolute value of the exciton concentration. The electrochemical potential drop associated with minority carrier diffusion through the base decreases with increasing exciton concentration. Therefore, it is desirable to form the base region with a narrow bandgap material, that is, a material with a high intrinsic carrier concentration, and high impurity doping with the relative impurity/intrinsic carrier concentration large. For an NPN transistor, it is desirable to have a high acceptor doping concentration in the base to create a negative chemostatic potential energy, resulting in a large recombination velocity enhancing a large gradient of mobile electrons transiting the base with a high diffusion velocity.

A heavily acceptor doped region has the additional advantage of reducing the base de-biasing resistance. This increases the total minority carrier flux through the base, and increases the transistor current density capability. Unfortunately, at high impurity atom concentrations, the band structure is altered such that bandgap narrowing occurs and the chemostatic potential self-limits. Furthermore, increasing the magnitude of the base chemostatic potential tends to reduce minority carrier injection into the base, which degrades transistor performance. The relative minority carrier injection across a junction is related to the relative chemostatic potential magnitude. This injection efficiency can be improved by increasing the magnitude of the emitter chemostatic potential (opposite polarity of the base chemostatic potential). This effect is limited by emitter bandgap narrowing at high polaron concentrations.

Preferential minority carrier injection is due to the relative chemostatic potential magnitude with higher minority carrier injection into neutral region of lower chemostatic potential magnitude. Minority carrier diffusion is favored in regions of high recombination velocity, presuming a region of high chemostatic potential magnitude with the proper boundary conditions. In order to obtain a high diffusion flux it is desirable to have a low recombination velocity at the boundary of the injection source (the emitter) and a high recombination velocity at the collector boundary. In a transistor biased in the active region, the reverse biased junction at the collector-base boundary provides the high boundary recombination velocity required due to the large potential for minority carriers. It is desirable to establish a vanishing recombination velocity in the emitter to eliminate any diffusion current into the emitter and to provide all emitter transport by majority carrier drift. Therefore, it appears desirable to have an emitter void of recombination, commensurate with a region of high chemostatic potential magnitude.

In U.S. Pat. No. 2,569,347 mentioned above, two methods of enhancing the emitter chemostatic potential are predicted, first, increased impurity atom concentration, i.e. increased polaron concentration, and second, increased bandgap energy, i.e. reduced exciton concentration. Substantially reduced emitter diffusion current presumes a combination of high donor doping concentration or wide bandgap energy along with low boundary recombination velocity at the emitter contact, which is characteristic of a low exciton concentration. Thus, the ideal transistor is characterized by a relatively large emitter/base chemostatic potential magnitude ratio, with a low recombination rate at the emitter boundary and a high recombination rate at the collector boundary. The emitter has a moderate polaron concentration and a very low exciton concentration due to a wide bandgap energy. The base has a narrower bandgap energy and a high acceptor doping concentration to maintain a lower chemostatic potential magnitude relative to the emitter. Thus, minority carrier injection into the emitter and minority carrier recombination in the emitter are both substantially reduced. This provides a very low emitter recombination velocity which favors majority carrier transport by drift. For a wide bandgap emitter heterojunction transistor, majority carrier transport in the emitter is favored, minority carrier injection into the emitter is substantially reduced, minority carrier injection into the base is enhanced, minority carrier diffusion in the base region is enhanced, and ohmic base debiasing is reduced. This should result in a large emitter-collector electron flux for an NPN transistor, with a small base hole flux which allows for a high gain device with good switching characteristics. Compound semiconductor devices, such as AlGaAs/GaAs transistors, operate on this principle. Unfortunately, full performance has not been realized to date.

SUMMARY OF THE INVENTION

In accordance with a broad aspect of the invention, a heterojunction transistor is presented which includes a highly acceptor doped compositional hybrid superlattice base of sub-micron thickness and of independently controlled polaron concentration and bandgap energy. A two zone emitter has a monocrystalline or semimetal film with donor concentration immediately adjacent the base, with a wider bandgap energy than the base. The emitter has a low recombination velocity to minimize minority carrier diffusion and to set the divergence of emitter and base carrier velocities. The transition region between the base and emitter acts as an anisotype heterojunction. A collector is provided, configured similarly to the emitter to permit control and optimization of the cut-in voltage, the collector having a semimetal boundary which isolates the transistor from underlying substrate effects. A low impedance substrate collector contact, a semimetal base contact, and a mesa isolated isotype semimetal emitter contact are provided to establish contact to the transistor.

In accordance with another broad aspect of the invention, a method for making a heterojunction transistor is presented. The method includes forming a base of sub-micron thickness of a superlattice of alternating silicon and silicon-germanium alloys doped with acceptor atoms. A monocrystalline film emitter with a low recombination velocity is formed, with a donor concentration adjacent the base establishing a chemostatic potential magnitude greater than the base chemostatic potential magnitude without degeneracy, whereby the junction between the base and the emitter is an anisotype homojunction and the transition region acts as an anisotype heterojunction. A collector is formed in a manner similar to the emitter, with a low recombination velocity, the collector having a donor concentration adjacent the base to establish a chemostatic potential magnitude greater than the base chemostatic potential magnitude without degeneracy, whereby the junction between the base and the collector is an anisotype homojunction and the transition region acts as an anisotype heterojunction.

BRIEF DESCRIPTION OF THE DRAWINGS

The invention is illustrated in the accompanying drawings, in which.

Figure 1:
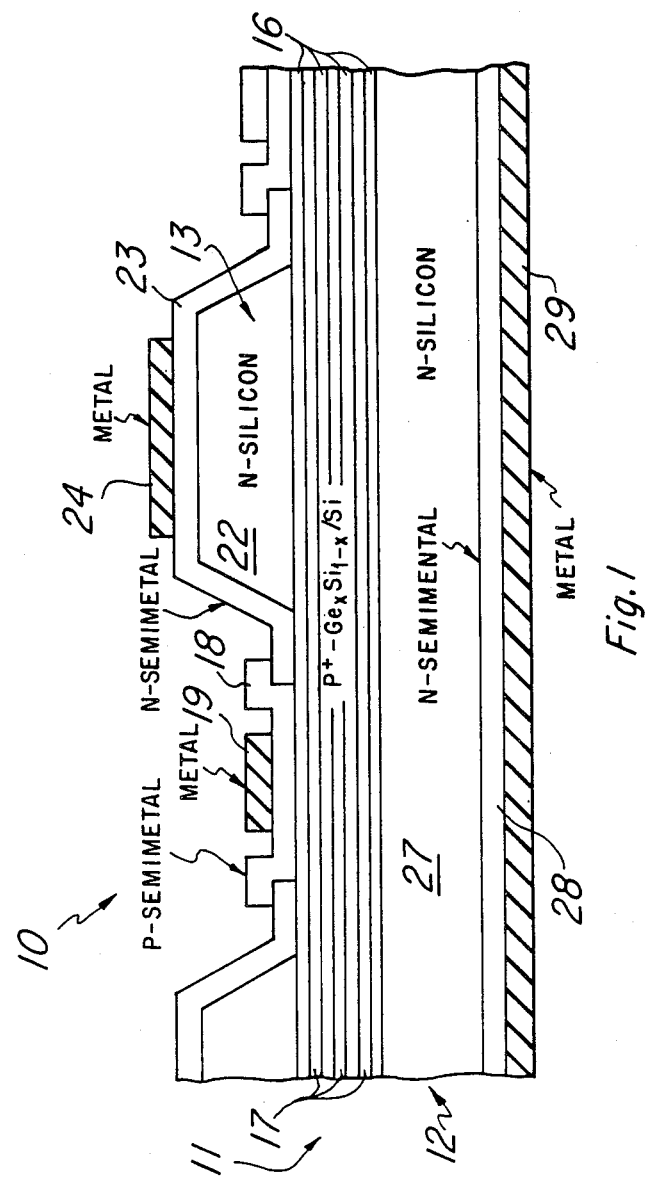
FIG. 1 is a side elevational cross-sectional view of an NPN heterojunction transistor fabricated in accordance with a preferred embodiment and method of the invention.

In the drawing, the sizes and dimensions of the various parts have been exaggerated or distorted for ease of description and clarity of illustration.

DETAILED DESCRIPTION OF THE PREFERRED EMBODIMENTS

With reference to FIG. 1, an NPN transistor 10 fabricated in accordance with a preferred method and embodiment of the invention is illustrated. Although an NPN transistor is shown, it is understood that the principles of the invention are equally applicable to PNP transistors equally well.

I believe that classical transistor approaches fail to fully embrace the importance of mobile carrier velocity divergence in the emitter and base regions. This effect is more pronounced as the disparity in chemostatic potential magnitudes increases in the neutral regions forming the emitter-base junction. A high mobile carrier diffusion velocity is built into the base, and a low diffusion velocity is built into the emitter. Mobile electrons drift through the emitter due to an externally applied field, while electrons travel through the base due to the built-in diffusion field. At low bias voltages, the emitter drift velocity is lower than the base diffusion velocity. The divergence in emitter and base mobile carrier velocities precludes a continuous mobile electron flux in the emitter and base due to conversation of charge considerations.

The base-emitter space charge region recombination is enhanced to establish a continuous current mechanism while the emitter drift field builds up with increasing base-emitter forward bias. This causes an equal base and emitter current with zero collector current, due to zero electron flux in the base. When the emitter drift field reaches sufficient strength that divergence of emitter electron drift velocity and the base mobile electron diffusion velocity vanishes, minority carrier injection into the base commences. This bias voltage is termed the "junction cut-in voltage". For bias voltages greater than the junction cut-in voltage, the collector current increases essentially exponentially with bias voltage. The space charge region recombination continues to be a strong influence and dominates the transistor gain, albeit with decreasing influence. The effect of the space charge recombination is to continually compensate for a lagging emitter recombination velocity rate with respect to the base recombination velocity rate with increasing bias.

At a precise forward bias, the rate of increase in emitter mobile carrier drift velocity equals the rate of increase in base mobile carrier diffusion velocity. This bias voltage is termed the "roll-off voltage". For bias voltages greater than the roll-off voltage, the emitter mobile carrier drift velocity has a greater rate of change with increasing applied bias than that of the base diffusion velocity. Hence, for bias voltages increasingly greater than the roll-off voltage, the space charge recombination effects diminish and vanish in the limit with the emitter recombination velocity becoming the gain limiting factor. The potential barrier reflecting minority carriers in the emitter reduces and the emitter boundary recombination effects become dominant. The peak transistor gain occurs at the roll-off bias voltage.

The collector current at which the roll-off voltage occurs is a function of the inherent divergence in emitter and base diffusion velocities, and hence, is related to the divergence of the base and emitter chemostatic potential magnitudes.

There are several ramifications of this with respect to classical heterojunction transistor theory: large base-emitter diode cut-in voltages, large offset voltages, and reduced gain. The cut-in voltage is a strict function of the divergence of the base and emitter chemostatic potential magnitudes. For identical chemostatic potential magnitudes in the surrounding neutral regions, the cut-in voltage is zero. As the emitter chemostatic potential magnitude becomes increasingly larger than that of the base, then the junction cut-in voltage correspondingly increases. Hence, for a wide bandgap emitter transistor, as proposed by classical theory, there will exist a large base-emitter cut-in voltage.

When the divergence of the base and emitter chemostatic potential magnitude is small, that is when the junction cut-in voltage is small, then the roll-off voltage occurs at low bias voltages and the emitter recombination velocity dominates the transistor gain characteristics with minimal space charge recombination effects. On the other hand, large divergence in base and emitter chemostatic potential magnitude, that is, large junction cut-in voltages, results in a roll-off voltage at high bias voltages. In fact, in a wide bandgap emitter heterojunction transistor it is possible that the roll-off voltage is never reached in the usable transistor bias range and the peak gain is never achieved with the transistor gain being dominated by space charge region recombination in all bias conditions. The peak gain at the roll-off voltage varies in absolute magnitude due to the magnitude of the rate limiting recombination velocities at the roll-off bias voltage. Maximum peak gains occur, with rapid roll-off, for low emitter recombination velocity and low divergence of base and emitter chemostatic potential magnitudes. Lesser peak gain magnitudes occur, with a gradual roll-off, for low emitter recombination velocity and a large divergence of base and emitter chemostatic potential magnitudes.

Hence, the transistor gain and roll-off voltage can be controlled by the relative divergence in base and emitter chemostatic potential magnitudes and the emitter recombination velocity, with secondary considerations such as base thickness, absolute base chemostatic potential magnitude, built-in field gradients, and the like.

Some applications, such as digital switching, or the like, require high gain at low current densities. Other applications, such as power transistors, or the like, are insensitive to low current gain, and primarily operate in a high bias, high current density configuration where a high roll-off voltage is desirable. It is most difficult to control the roll-off voltage, the cut-in voltage, and the gain with conventional planar, compensated wafer processing techniques, since control of the chemostatic potential and the emitter recombination velocity is difficult as a result of crystal perturbation associated with interstitial effects of excess impurity atoms. The internal recombination velocities are constrained independently of boundary conditions due to crystal damage and associated band structure perturbation. However, as will become apparent from the detailed description of the invention below, non-planar, non-compensated wafer processing techniques, such as molecular beam epitaxy or metal organic chemical vapor deposition, permit control of these transistor parameters. The offset voltage is due to the difference in cut-in voltages of the base-emitter and base-collector diodes. Since the base-emitter cut-in voltage is much higher, the offset voltage results by Kirchoff's law. This can be alleviated by a double heterojunction structure with each junction rectifying characteristics controlled by these considerations, described below in detail.

In order to optimize the device transport phenomena, it is important to independently control the polaron concentration, chemostatic potential, and recombination velocity of each neutral region surrounding a junction. For economic reasons, it is preferable to implement this crystal concept with a silicon-based wafer processing technique. For reasons previously delineated, it is desirable to fabricate the base with a high acceptor concentration and with a concurrently high intrinsic carrier concentration. This enhances electron injection into the base region and allows a steep diffusion gradient, high electron diffusion velocity, and high electron flux at low voltages. It is further desirable to make the base as thin as possible.

Thus, in accordance with the invention, the base 11 of the NPN transistor 10 is formed on a layer 12 of N type epitaxial silicon which forms the collector of the transistor, as below described. The base 11 has a high acceptor concentration and a high intrinsic carrier concentration to enhance electron injection into the base and to establish a steep diffusion gradient, high electron diffusion velocity, and high electron flux at low voltages. The base 11 is made to be as thin as possible, for example, of sub-micron thickness, and is constructed as a compositional hybrid superlattice of alternating layers 16 and 17 of silicon and silicon-germanium alloys, respectively, both heavily doped with boron acceptor atoms.

Although the layers 16 and 17 of the base 11 can be fabricated by any number of suitable techniques, a preferred method which enables atomic control is by molecular beam evaporation of germanium and silicon with direct, low energy implantation of boron in a silicon-based molecular beam evaporation (MBE) system (not shown). Thus, with continuous silicon evaporation and periodically, abruptly shuttering germanium co-evaporation with continuous low energy boron ion implantation with concentrations exceeding $10^{20}$ atoms/cm$^3$, then an isotype strained layer superlattice of $Ge_xSi_{1-x}$ and Si is fabricated.

A germanium-silicon lattice mismatch induces a local strain which remains commensurate and strained up to a certain thickness for each value of x, beyond which the strain becomes excessive and the alloy relaxes due to the formation of dislocations. The thickness for which the alloy relaxes decreases for increasing proportions of germanium. All of the strain occurs in the $Ge_xSi_{1-x}$, not in the clad silicon, with the dislocation network originating at the interface of the $Ge_xSi_{1-x}$ and clad silicon. By repetition of $Ge_xSi_{1-x}$ and Si films, as shown, each possibly several atoms thick, a strained layer superlattice up to a micron thick can be formed with a substantially lower chemostatic potential than an equivalently doped silicon region. The germanium atoms are isoelectronic with respect to silicon but provide recombination sites between the silicon conduction and valence bands. The effective bandgap energy and intrinsic carrier concentration can be independently set with respect to the doping concentration by controlling the value of x in the $Ge_xSi_{1-x}$ and by controlling the relative thicknesses of the $Ge_xSi_{1-x}$ and clad Si.

Since the base 11 is highly acceptor doped, it is virtually immune from etching by typical anisotropic silicon etchants, such as propanol diluted potassium hydroxide; consequently, the use of such anisotropic silicon etchants is of particular advantage in establishing a base contact to a such thin bases region as described above. The compositional hybrid superlattice base 11, as described, allows independent control of polaron concentration and bandgap energy, and therefore, chemostatic potential.

The base 11 is terminated by a P isotype semimetal layer 18, for example, such as described in copending patent application Ser. No. 876,322, filed June 18, 1986, entitled "SEMIMETAL SEMICONDUCTOR CONTACT", by Patrick A. Curran, the inventor hereof, said application being assigned to the assignee hereof, and incorporated herein by reference, as background. The semimetal layer 18 is acceptor and oxygen doped microcrystalline silicon deposited in a silicon-based MBE with a thin overlying undoped monocrystalline silicon film patterned in the desired contact regions. By adjusting the acceptor and oxygen concentration, the chemostatic potential of the semimetal layer 18 can be altered to control the boundary recombination velocity of the base, in the manner described in said copending patent application Ser. No. 876,322. An overlying metal contact 19 contacts the semimetal layer 18 without altering the boundary recombination velocity of the base 11.

A two zone emitter 13 is fabricated on the base 11, with an effectively wider bandgap energy than the base 11, and with a low recombination velocity to minimize minority carrier diffusion and maintain sufficient control to set the divergence between the emitter and base carrier velocities. The two zone emitter 13 has a substantially monocrystalline film 22 with the proper donor concentration formed immediately adjacent to the base region 11, and an overlying N semimetal region 23. Since the base 11 is an acceptor doped, compositional hybrid superlattice with clad monocrystalline silicon at the metallurgical junction between the base 11 and emitter 13, the junction is an anisotype homojunction, but the transition region acts as an anisotype heterojunction. The emitter donor concentration is established so that the chemostatic potential magnitude of the emitter 13 is greater than the effective chemostatic potential magnitude of the base 11, but without the onset of degeneracy. Thus, with the base doping concentration established as described above, a maximum emitter monocrystalline donor concentration can be about $10^{18}$ atoms/cm$^3$, but can be varied to modify the roll-off voltage and peak gain operating conditions.

As shown, the emitter 13 is terminated by an isotype semimetal layer 23, for example, such as described in the aforementioned copending patent application Ser. No. 876,322. The semimetal layer 23 is donor and oxygen doped microcrystalline silicon deposited in a silicon-based MBE with a thin overlying undoped monocrystalline silicon film patterned in the desired contact regions. By adjusting the donor and oxygen concentration, the chemostatic potential of the semimetal layer 23 can be altered to control the emitter boundary recombination velocity, in the manner described in said copending patent application Ser. No. 876,322. An overlying metal contact 24 contacts the semimetal layer 23 without altering the boundary recombination velocity of the emitter 13. The vertical charge transport through the semimetal layer 23 is enhanced with concurrent design control of the boundary recombination velocity of the emitter 13 to realize the theoretical aspects of this invention.

It should be noted that the portions of the semimetal layer 23 bounding the emitter but which do not lie below the metal of the metal contact 24 do not transmit charge to the monocrystalline emitter but nevertheless maintain the proper emitter boundary recombination velocity.

Thus, the composite emitter 13 in accordance with the invention, has a chemostatic potential magnitude greater than that of the base 11, favoring electron injection into the base with a favored transmission of electrons from the emitter contact by a drift field and high reflection of holes injected into the emitter from the base. These phenomena can be sufficiently established to cause the bias controlled junction currents to be dominated by space charge region recombination effects due to large divergence of emitter and base mobile carrier velocities. By appropriately increasing the emitter recombination velocity the recombination effects can be adjusted to obtain the desired cut-in voltage, roll-off voltage, and peak gain operating point. Two ways by which this this can be accomplished are as follows. One way is to control the emitter boundary recombination velocity by varying the emitter semimetal isotype Schottky barrier height by adjusting the semimetal donor and oxygen concentrations. The other way to control the emitter recombination velocity is by providing germanium counter-doping in the emitter monocrystalline region by concurrent donor and germanium low energy implantation during silicon evaporation in the UHV silicon-based MBE. The isoelectronic germanium atoms effectively increase the silicon midband traps, augmented by the compressive stress associated with the larger germanium atom in the silicon lattice. The germanium atoms are fully activated with the donor atoms by rapid thermal annealing. This has the effect of raising the intrinsic carrier concentration. Moreover, a recombination velocity gradient can be realized by spatially varying the germanium implant dose during UHV silicon evaporation.

The collector 12 is configured in a similar manner as the emitter 13, with independent control to permit control and optimization of the transistor parameters.

Thus, the collector 12 is formed in a ultra high vacuum molecular beam evaporation deposition chamber, with an bandgap energy effectively wider than the base 11, and with a low recombination velocity. The collector 12 has a substantially monocrystalline layer 27 with the proper donor concentration formed immediatley adjacent to the base region 11. Like the emitter-base junction, the collector-base metallurgical junction is an anisotype homojunction, but acts as an anisotype heterojunction. The collector donor concentration is established so that the chemostatic potential magnitude of the collector 12 is greater than the effective chemostatic potential magnitude of the base 11, Thus, with the base doping concentraiton established as described above, a maximum collector monocrystalline donor concentration can be about $10^{18}$ atoms/cm$^3$, but can be varied to adjust the transistor operating conditions, as desired.

As shown, the collector 12 is terminated by an N isotype semimetal layer 28, for example, such as described in the aforementioned copending patedint application Ser. No. 876,322. The semimetal layer 28 is donor and oxygen doped microcrystalline silicon deposited in a silicon-based MBE, with a thin underlying undoped monocrystalline silicon film to which contact can be made. Again, by adjusting the donor and oxygen concentration, the chemostatic potential of the semimetal layer 28 can be altered to control the collector boundary recombination velocity, in the manner described above, and in said copending patent application Ser. No. 876,322. A metal contact 29 contacts the semimetal layer 28 without altering the boundary recombination velocity of the collector 12. The vertical charge transport through the semimetal layer 28 is enhanced with concurrent design control of the boundary recombination velocity of the collector 12 to realize the theoretical aspects of this invention.

Thus, the collector 12 in accordance with the invention, has a chemostatic potential magnitude greater than that of the base 11. Again by appropriately adjusting the collector recombination velocity the recombination effects can be adjusted to obtain the desired transistor parameters.

It will be apparent that the entire double heterojunction structure can readily be fabricated in single operation in a ultra high vacuum deposition chamber configured with two E-beam evaporators and two low energy ion implanters with dual sources. The collector can be contacted by a low impedance substrate contact. The base can be contacted by means of a plasma etching of the emitter semimetal followed by an anisotropic silicon etch with the semimetal as the etch mask. The emitter can be contacted on the planar surface and is mesa isolated. All regions can be fabricated to yield the desired operating conditions under computer control in a high precision silicon-based MBE apparatus.

Figure 2:
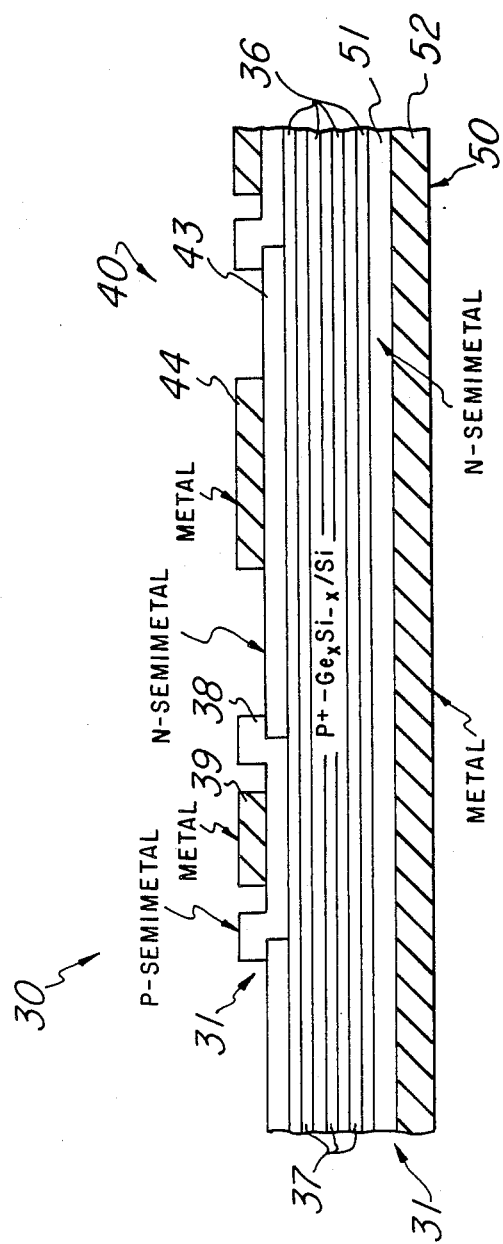
FIG. 2 is a side elevational cross-sectional view of an NPN heterojunction transistor fabricated in accordance with another preferred embodiment and method of the invention.

With reference now to FIG. 2, an NPN transistor 30 fabricated in accordance with another preferred method and embodiment of the invention is illustrated. Again, although an NPN transistor is shown, the transistor could be fabricated as a PNP transistor.

The base 31 of the transistor 30 is fabricated in a manner similar to the base 12 described above with respect to FIG. 1, and is a compositional hybrid superlattice of sub-micron thickness of alternating layers 36 and 37 of silicon and silicon-germanium alloys, respectively, heavily doped with boron acceptor atoms. The base 31 has a high acceptor concentration and a high intrinsic carrier concentration.

As above described, the base 31 can be fabricated by molecular beam evaporation of germanium and silicon with direct, low energy implantation of boron in a silicon-based molecular beam evaporation (MBE) system. Again, with continuous silicon evaporation and periodically, abruptly shuttering germanium co-evaporation with continuous low energy boron ion implantation with concentrations exceeding $10^{20}$ atoms/cm$^3$, then an isotype strained layer superlattice of $Ge_xSi_{1-x}$ and Si is fabricated, as shown.

The base 31 is terminated by a P isotype semimetal layer 38, for example, such as described in said copending patent application Ser. No. 876,322. The semimetal layer 38 is acceptor and oxygen doped microcrystalline silicon deposited in a silicon-based MBE with a thin overlying undoped monocrystalline silicon film pattern in the desired contact regions. By adjusting the acceptor and oxygen concentration, the chemostatic potential of the semimetal layer 38 can be altered to control the boundary recombination velocity of the base, in the manner described above and in said copending patent application Ser. No. 876,322. An overlying metal contact 39 contacts the semimetal layer 38 without altering the boundary recombination velocity of the base 31.

In the embodiment of FIG. 2, a one zone emitter 40 is shown fabricated directly on the base 31, the emitter being an overlying isotype N semimetal region 43, for example, such as described in the aforementioned copending patent application Ser. No. 876,322. The semimetal layer 43 is donor and oxygen doped microcrystalline silicon deposited in a silicon-based MBE. By adjusting the donor and oxygen concentration, the chemostatic potential of the semimetal layer 43 can be altered to control the emitter boundary recombination velocity, in the manner described in said copending patent application Ser. No. 876,322. An overlying metal contact 44 contacts the semimetal layer 43 without altering the boundary recombination velocity of the emitter 40.

The collector 50 is configured in a similar manner as the emitter 40, being in a ultra high vacuum molecular beam evaporation deposition chamber, with an bandgap energy effectively wider than the base 31, and with a low recombination velocity. The collector 50, as shown, includes an N isotype semimetal layer 51, for example, such as described in the aforementioned copending patent application Ser. No. 876,322. The semimetal layer 51 is donor and oxygen doped microcrystalline silicon deposited in a silicon-based MBE, with a thin underlying undoped monocrystalline silicon film to which contact can be made. Again, by adjusting the donor and oxygen concentration, the chemostatic potential of the semimetal layer 51 can be altered to control the collector boundary recombination velocity, in the manner described above, and in said copending patent application Ser. No. 876,322. A metal contact 52 contacts the semimetal layer 51 without altering the boundary recombination velocity of the collector 50.

The collector 50 has a chemostatic potential magnitude greater than that of the base 31. Again by appropriately adjusting the collector recombination velocity the recombination effects can be adjusted to obtain the desired transistor parameters.

Although the invention has been described and illustrated with a certain degree of particularity, it is understood that the present disclosure has been made by way of example only and that numerous changes in the combination and arrangement of parts or steps may be resorted to by those skilled in the art without departing from the spirit and the scope of the invention as hereinafter claimed.

What is claimed is:

1. A heterojunction transistor comprising:
a highly acceptor doped compositional hybrid superlattice base region of sub-micron thickness;
a semimetal emitter on one side of said base,
a semimetal collector on another side of said base;
and a semimetal base contact in contact with said base.

2. The transistor of claim 1 wherein the emitter has a chemostatic potential magnitude greater than the base to favor electron injection into the base with a favored transmission of electrons from the emitter contact by a drift field and reflection of holes injected into the emitter from the base, whereby bias controlled junction currents are dominated by space charge regions recombination effects due to large divergence of emitter and base mobile carrier velocities.

3. The transistor of claim 1 in which the desired cut-in voltage, roll-off voltage, and peak gain operating point are established by increasing the emitter recombination velocity.

4. The transistor of claim 3 in which the emitter recombination velocity is increased by varying the emitter semimetal isotype Schottky barrier height by adjusting the semimetal donor and oxygen concentrations.

5. A heterojunction transistor comprising:
a highly acceptor doped compositional hybrid supperlattice base region of sub-micron thickness whereby polaron concentration and bandgap energy are independently controlled;
a two zone emitter having a substantially monocrystalline film with a donor concentration adjacent the base, the emitter having a wider bandgap energy than the base and having a low recombination velocity to minimize minority carrier diffusion and to set the divergence of emitter and base carrier velocities, whereby a transition region between said emitter and said base acts as an anisotype heterojunction;
a collector having a substantially monocrystalline film with a donor concentration adjacent the base opposite said emitter, the collector having a wider bandgap energy than the base and having a low recombination velocity, whereby a transition region between said base and said collector acts as an anisotype heterojunction, whereby the cut-in voltage can be controlled;
a semimetal collector boundary which isolates the transistor from underlying substrate effects;
a semimetal base contact;
and a mesa isolated semimetal emitter zone having an OHMIC contact thereto.

6. The transistor of claim 5 wherein the emitter contact is a donor and oxygen doped microcrystalline film patterned in desired contact regions.

7. The transistor of claim 5 wherein the monocrystalline emitter donor concentration establishes an emitter chemostatic potential magnitude greater than the base chemostatic potential magnitude.

8. The transistor of claim 7 in which a maximum emitter monocrystalline donor concentration is $10^{18}$ atoms/cm$^3$.

9. The transistor of claim 7 in which the emitter monocrystalline donor concentration establishes roll-off voltage and peak gain operating conditions.

10. The transistor of claim 7 in which the composite emitter has a chemostatic potential magnitude greater than the base to favor electron injection into the base with a favored transmission of electrons from the emitter contact by a drift field and reflection of holes injected into the emitter from the base, whereby bias controlled junction currents are dominated by space charge regions recombination effects due to large divergence of emitter and base mobile carrier velocities.

11. The transistor of claim 10 in which the desired cut-in voltage, roll-off voltage, and peak gain operating point are established by increasing the emitter recombination velocity.

12. The transistor of claim 11 in which the emitter recombination velocity is increased by varying the emitter semimetal isotype Schottky barrier height by adjusting the semimetal donor and oxygen concentrations.

13. A heterojunction transistor comprising:
a highly acceptor doped compositional hybrid superlattice base region of sub-micron thickness whereby polaron concentration and bandgap energy are independently controlled;
a two zone emitter having a substantially monocrystalline film with a donor concentration adjacent the base to establish a chemostatic potential magnitude greater than the base chemostatic potential magnitude, said emitter being counter doped with germanium to increase the recombination velocity, having a wider bandgap energy than the base, and having a low recombination velocity to minimize minority carrier diffusion and to set the divergence of emitter and base carrier velocities, whereby a transition region between said emitter said base acts as an anisotype heterojunction;
a collector having a substantially monocrystalline film with a donor concentration adjacent the base opposite said emitter, the collector having a wider bandgap energy than the base, and having a low recombination velocity whereby a transition region between said base and collector acts as an anisotype heterojunction, whereby the cut-in voltage can be controlled;
a semimetal collector boundary which isolates the transistor from underlying substrate effects;
a semimetal base contact; and
a mesa isolated semimetal emitter zone, having an ohmic contact thereto;
the chemostatic potential magnitude of said two-zone emitter favoring electron injection into the base with a favored transmission of electrons from the emitter contact by a drift field and minority carrier injection into the base, whereby bias controlled junction currents are dominated by space charge region recombination effects due to large divergance of emitter and base mobile carrier velocities.

14. The transistor of claim 13 in which the germanium counter doping is spatially varied, whereby a recombination velocity gradient is realized.

* * * * *